United States Patent [19]
Carter et al.

[11] Patent Number: 4,791,251
[45] Date of Patent: Dec. 13, 1988

[54] DELAYED ACTUATOR WITH VISCO-ELASTIC TIMER

[75] Inventors: Robert E. Carter, Auburndale, Mass.; Porter Stone, Walpole, N.H.

[73] Assignee: Piezo Electric Products, Inc., Cambridge, Mass.

[21] Appl. No.: 54,415

[22] Filed: May 26, 1987

Related U.S. Application Data

[63] Continuation-in-part of Ser. No. 940,803, Dec. 12, 1986, Pat. No. 4,742,189.

[51] Int. Cl.[4] .......................... H01H 7/00; F22B 1/28; G04C 23/00; A01G 27/00
[52] U.S. Cl. ..................... 200/33 R; 219/271; 219/272; 222/638; 239/70
[58] Field of Search ............ 200/33 R, 34, 52 R, 200/61.58 R; 73/150 A; 222/638–652; 267/113, 114, 215, 259, 260; 239/70, 99; 219/214, 271, 272, 273, 276, 507

[56] References Cited

U.S. PATENT DOCUMENTS

| | | | |
|---|---|---|---|
| 2,755,349 | 7/1956 | Silvers | 200/33 R |
| 3,471,659 | 10/1969 | Ferrara | 200/33 R |
| 3,907,493 | 9/1975 | Thettu | 219/496 X |
| 4,005,858 | 2/1977 | Lochner | 267/259 X |
| 4,702,418 | 10/1987 | Carter et al. | 239/101 |
| 4,742,189 | 5/1988 | Carter et al. | 200/33 R |

*Primary Examiner*—J. R. Scott
*Attorney, Agent, or Firm*—Joseph S. Iandiorio; Douglas E. Denninger

[57] ABSTRACT

A delayed actuator mechanism with visco-elastic timer is provided including a support section and an actuator section mounted to the support section. A compression spring biases the actuator section in a first state and permits the actuator section to be selectively switched to a second state. In that state a cocked torsion spring urges a detent carried by the actuator into engagement with a shoulder of the support section to restrain the actuator section in the second state. A visco-elastic delay mechanism gradually relaxes the torsion spring until the compression spring overcomes the detent shoulder restraint to abruptly switch the actuator section to the first state.

31 Claims, 5 Drawing Sheets

DELAYED ACTUATOR WITH VISCO-ELASTIC TIMER

RELATED APPLICATION

This application is a continuation-in-part of U.S. Ser. No. 940,803, filed Dec. 12, 1986, now U.S. Pat. No. 4,742,189, "Visco-Elastic Delayed Actuator", by Carter et al.

FIELD OF INVENTION

This invention relates to a delayed actuator with a visco-elastic timer and more particularly to a mechanism which operates devices such as relays, valves and fluid dispensers by temporarily holding such devices in a first state for a visco-elastically controlled duration and then abruptly and automatically switching them to a second state.

BACKGROUND OF INVENTION

Time delayed actuators are widely employed to switch relay contacts, open and close fluid control valves and operate many other types of mechanisms. Electrical and electronic timers are perhaps the most commonly used devices of this type. In certain applications, however, such timers are impractical because of their expense, complexity and/or need for a power supply.

As an alternative to the electrical timer a dashpot type of delayed actuator may be utilized. This mechanism includes a piston disposed within a fluid filled cylinder. As the piston is moved through the cylinder fluid is forced through a circumferential gap between the piston and the cylinder wall so that the piston gradually changes from a first state to a second state.

A rotary plate delayed actuator is used to slow the motion of cassette tape machine doors and record player armatures. This device employs a pair of parallel plates that are separated by a layer of viscous fluid. Torque is applied to one of the plates while the other is held fixed and the viscous drag of the fluid slows the motion of the movable plate.

Typically, dashpot and rotary plate devices are effective for providing delays of only a few seconds. In order to extend their delay periods their fluid reservoirs must be made impractically large. Increasing the delay of the dashpot device alternatively requires making the circumferential gap exceedingly and impractically small. Moreover, both devices must be hermetically sealed to prevent escape or contamination of the fluid. And each requires at least one precision tolerance (i.e., the dashpot piston/cylinder clearance and the rotary plate spacing) which adds significantly to the cost of the device.

There is a particular need for an inexpensive and effective time delayed actuator mechanism for dispensing of fragrances, insecticides and other airborne fluids. Present dispensers are typically either passive or active. Passive devices employ a container filled with a fluid. A wick protruding from the fluid filled container absorbs the fluid and emits it into the air. These systems do not employ extremely volatile fluids because such fluids evaporate too rapidly. However, as a result, the emission rate of these devices is often not sufficient to perform the function desired, e.g., the elimination of offensive odors.

Less volatile fluids may be dispensed more effectively with an active device that employs an electric blower or heater to stimulate emission. However, such devices are fairly expensive and again require a source of electrical power.

The applicants herein have previously provided another timer which uses a visco-elastic adhesive to temporarily hold an actuator in a first state. See copending U.S. patent application Ser. No. 940,803, Visco-elastic Delayed Actuator, filed Dec. 12, 1986. After a timed duration dependent upon the strength of the visco-elastic material the adhesive releases the actuator so that it suddenly switches to a second state. Although this device does provide for significantly increased timing periods and is effective in a variety of devices such as relays, fluid dispensers and valves, the size, weight and force on the actuator it employs is limited by the holding strength of the visco-elastic adhesive.

SUMMARY OF INVENTION

It is therefore an object of this invention to provide a delayed actuator mechanism which is relatively uncomplicated and simple to manufacture and operate and which does not require a source of electricity, precision parts or a hermetic seal.

It is a further object of this invention to provide a delayed actuator mechanism that remains in a first state for extended periods of time and to then rapidly, reliably and automatically switches to a second state virtually instantaneously at the end of the timing cycle.

It is a further object of this invention to provide a delayed actuator that is effective for operating a wide variety of fluid dispensers, valves, relays and other mechanisms.

It is a further object of this invention to provide a delayed actuator that enables a fluid dispenser to dispense effective amounts of fluid only as needed for timed durations.

It is a further object of this invention to provide a delayed actuator that achieves prolonged time delays for large and/or heavy mechanisms.

It is a further object of this invention to provide a delayed actuator with a visco-elastic timer which exhibits an actuator holding force that is not dependent on the strength of the visco-elastic adhesive.

This invention results from the realization that an improved time delayed actuator mechanism with an extended time delay may be provided by utilizing a visco-elastic adhesive timer to delay operation of the actuator so that it remains in a first state for a large portion of the timed cycle and then relatively rapidly switches to a second state. The invention results from the further realization that improved actuator holding force which is independent of visco-elastic adhesive strength and improved, virtually instantaneous switching are achieved by employing the adhesive only as a timer and utilizing entirely distinct means for retaining the actuator in a temporary state.

This invention features a delayed actuator mechanism with a visco-elastic timer including a support section and an actuator section mounted to the support section. There are biasing means for urging the actuator section into a first state and permitting the actuator section to be selectively switched to a second state. There are also means for restraining the actuator section in the second state and visco-elastic delay means for gradually releasing the means for restraining until the biasing means overcomes the means for restraining to abruptly switch the actuator section to the first state.

In a preferred embodiment, the visco-elastic delay means includes a movable member and visco-elastic adhesive means interconnecting the movable member and the support section. The means for restraining may include means interconnecting the movable member and the actuator section and responsive to the actuator section being switched into the second state for urging the movable member to move gradually relative to the support section until the resilient biasing means suddenly overcomes the means for restraining to abruptly switch the actuator section to the first state. The means for restraining may further include a shoulder disposed in the support section and detent means carried by the actuator section for engaging the shoulder and restraining the actuator section in the second state. The movable member may include a rotor and the means for urging may include a torque biasing means responsive to the actuator being in the second state for applying torque to engage the detent means with the shoulder and urging the rotor to rotate gradually relative to the support section to relax the torque biasing means until the resilient biasing means suddenly overcomes the means for restraining to abruptly switch the actuator section to the first state. The torque biasing means may include a helical spring disposed about the actuator section. The biasing means may also include a helical spring disposed about the actuator section and interconnecting the actuator section and the support section. The actuator section may be axially slidably mounted in the support section and may be axially rotatably mounted in the support section for rotating to wind the torsion spring in the second state.

Preferably the support section includes a housing and the housing has a reservoir for containing a fluid and port means for dispensing the fluid. Typically, the port means is an area which is at least as large as the exposed area of the reservoir.

Means, responsive to the actuator section in one of the first and second states may be provided for accelerating vaporization of the fluid in the reservoir. Such means for accelerating may include a set of electrical contacts which are closed in response to the actuator section being in one of the first and second states to drive the means for accelerating and opened in response to the actuator section being in the other state to stop the means for accelerating.

Alternatively, closure means may be provided for closing to cover the port means in response to the actuator means being in one of the first and second states. Such closure means typically open to uncover the port means in response to the actuator means being in the other state. Preferably the closure means are pivotably mounted to the housing.

The means for restraining may include first gear means operably connected to and driven by the visco-elastic delay means and complementary second gear means connected to the actuator section and responsive to the biasing means for driving the first gear means until the second gear means disengages first gear means and the actuator section is abruptly switched to the first state. The support section may include compartment means with the movable member movably mounted in the compartment means and the visco-elastic means disposed in the compartment means about the operator member for delaying movement of the operator member. The first gear means may include a rotatable pinion gear and the second gear means may include rack means arranged longitudinally on the actuator section. The biasing means may include helical spring means disposed between the section and the actuator section. The movable member may be rotatably mounted in the compartment means and may include a paddle wheel device. The pinion gear means may be axially connected with the rotatable movable member for rotating therewith. The actuator section may be flexible for permitting the rack means to slide over the pinion gear means as the actuator section is switched from the first to the second state.

BRIEF DESCRIPTION OF THE DRAWINGS

Other objects, features and advantages will occur from the following description of a preferred embodiment and the accompanying drawings, in which.

DESCRIPTION OF THE PREFERRED EMBODIMENTS

A delayed actuator mechanism with a visco-elastic timer according to this invention includes a support section which is typically in the form of a plastic or metal housing. A preferred use for the actuator mechanism is as a timer for a fragrance or other fluid dispenser and in such devices the housing includes a reservoir for containing a fluid to be dispensed and vents or other port means for dispensing the fluid. The port means are typically provided with an area which is at least as large as the exposed area of the reservoir.

An actuator section is mounted to the housing and typically includes a knob or handle for operator access and an elongate section which is received within the housing. Preferably the actuator is axially slidable and rotatably mounted in the housing. It is constructed of a suitable plastic or metal material.

Biasing means such as a helical spring are disposed in the support section for urging the actuator section into a first state and permitting the actuator section to be selectively switched to a second state. Typically, a helical spring biasing means is wound about the actuator section and connects the actuator and the support section.

A mechanism is provided to temporarily restrain the actuator in the second state and visco-elastic delay means are provided to gradually release the restraining mechanism. For example, a movable member such as a rotating plate or rotor may be interconnected with the housing by a visco-elastic adhesive. The visco-elastic material typically comprises a sticky substance such as "Stick-Em" ™ brand mousetrap glue manufactured by T. F. Eaton and Company. A helical torsion spring or similar spring means interconnect the movable rotor and the actuator section. A detent is carried by the actuator and a complementary shoulder is disposed in the support section.

To set the actuator in the second state the operator grasps the handle and depresses the actuator while at the same time rotating the handle. The detent slides through a slot in the support section which includes the shoulder. Depressing and rotating the actuator in this manner winds the torsion spring. As a result, that spring applies torque to the actuator which engages the detent with the support shoulder. This holds the actuator in the depressed second state. At the same time the wound torsion spring exerts torque on the attached rotor and causes it to rotate relative to the support section. That rotation is hindered and prolonged by the viscous drag of the innerconnecting visco-elastic material. Eventually, the torsion spring unwinds sufficiently that the opposing force of the resilient biasing spring overcomes the restraining force of the shoulder on the detent means and forces the actuator suddenly upwardly into the first state. This switching time is virtually instantaneous relative to the time delay provided by the viscous delay means and the unwinding of the torsion spring.

The adhesiveness and viscosity of the adhesive are selected to provide the desired time delay, e.g., a stickier adhesive provides increased viscous drag, slower movement of the rotor and, as a result, a longer time delay. In order to provide time delays of hours or more the adhesive must exhibit elasticity even under strains on the order of thousands of a percent. By selecting a visco-elastic adhesive with suitable adhesion, rather than a viscous fluid without elastic properties, time delays of minutes to hours and even days may be provided. At the same time the electrical energy and intricate construction required by most conventional timers are eliminated.

Because the restraining means and not the visco-elastic adhesive holds the actuator in its second state, the adhesive does not hinder switching in any way and the actuator switches rapidly to the first state at the completion of the timing cycle. Moreover, the restraining force is determined by the strength of the torsion spring and detent and not by that of the adhesive. As a result, heavier relays, closures and other devices may be controlled for desired times without requiring a stronger adhesive. The adhesive serves only as a timer and yields equally effective results for actuators of all weights and sizes, and irrespective of the force to which they are subject.

Various types of fluid dispensing devices as well as valves, relay switches and other mechanisms may employ the delay mechanism of this invention. For example, in one fluid dispensing embodiment a closure is pivotably mounted to the housing for covering the ports in one of the first and second states. The actuator engages the closure to open the ports with the actuator in one of the first or second states. The fluid reservoir includes an absorbent wick which is impregnated, or fed by gravity, capillary action, pumps or other means, with a volatile liquid to be dispensed. With the ports open the fluid within the reservoir is free to diffuse and/or convect through the ports to the outside environment. To insure proper vaporization the fluid selected should be fairly volatile at room temperature.

In an alternative embodiment vaporization may be improved by utilizing a fan, heater, atomizer or similar device. This embodiment is accomplished by providing electrical contacts which are closed by the actuator in one of the first and second states and opened by the actuator in the other state. Closing the contact operates the vaporization enhancer whereas opening the contacts stops that device. When such an enhancer is utilized, a closure or louver doors are not required for the housing ports and a less volatile fluid may be employed. The electrical power source provided for this enhancer includes, for example, a battery such as a 1.5 volt flashlight cell or 9 volt transistor radio battery, or AC power from an external source.

A preferred vaporization enhancing device includes an electrically driven fan. In such a case the reservoir may be an absorbent pad or wick material which is impregnated with a volatile fluid. Alternatively, the device may comprise a heating element such as an electrical resistance heater. The heater is typically placed in intimate thermal contact with volatile fragrance compositions. In such a case the reservoir may include a thermally conductive plate which is either impregnated with or supplied with a fluid composition that is volatile at the temperature of the heating device. In still another embodiment the vaporization enhancing device may include a piezoelectric or other ultrasonic atomizer. The reservoir for this type of enhancer is typically a liquid which is volatile at room temperature and is delivered to the atomization site by a capillary or other pumping action such as gravity feed.

To insure that the closure or the electrical contacts are properly engaged and operated by the actuator a pusher plate or similar engagement member is fixed to the actuator for making engagement with the closure or contacts. Typically, the torsion spring is disposed between this engagement member and the rotor means and the biasing spring is disposed between the support section and the engagement member.

In an alternative embodiment, the actuator is restrained by a gear mechanism. For example, an elongate actuator shaft which is longitudinally movably mounted in the support section carries a rack proximate its lower end. A rotatable pinion gear which is engageable with the rack is axially or otherwise operably connected to the visco-elastic delay mechanism. A preferred delay mechanism includes a rotatable paddle wheel or other device which is movably mounted in a compartment within the support section. A visco-elastic adhesive such as is described above is disposed in the compartment around the movable member so that it interconnects the support section and the movable member. A helical spring or similar biasing device is disposed between the upper end of the actuator and the support section. The spring urges the actuator into an extended condition so that it actuates a switch, e.g., a toggle switch, microswitch or alternatively a valve, relay or similar device mounted in the support section. For example, in its extended state the actuator holds the toggle switch in a first, e.g. "off", state.

To operate this timer the actuator is retracted against the biasing spring. Typically, the actuator is composed of plastic or other flexible material so that as the actuator is retracted the rack teeth slide over the pinion teeth and, consequently, the operator does not have to rotate the pinion or overcome the drag of the visco-elastic material. In its retracted condition the actuator no longer engages the toggle switch and that switch is allowed to change into a second, e.g. "on", state. The helical spring or other resilient means bears against the actuator and slowly urges it back toward the extended condition. The speed of this return, and hence the length of the time duration, is controlled by selecting the viscosity of the adhesive material as described above. The return of the actuator to the first state is also restrained by the complementary rack and pinion mechanism. As the actuator is gradually extended the teeth of the rack engage the teeth of the pinion and the rack rotatably drives the pinion. This movement is slowed by the hindrance of the visco-elastic adhesive on the paddle wheel member. However, eventually the rack extends past and disengages the pinion. At this point the helical spring abruptly snaps the actuator back into the fully extended condition so that the toggle switch or other device is actuated.

Figure 1:
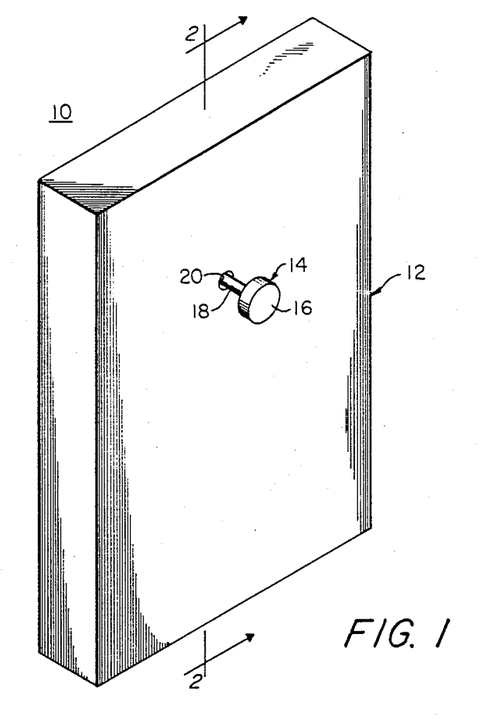
FIG. 1 is an axonometric view of a fluid dispenser utilizing the delayed actuator with visco-elastic timer according to this invention.

There is shown in FIG. 1 a visco-elastic delayed fluid dispenser 10 according to this invention. Dispenser 10 includes a support section housing 12 which has fluid dispensing ports on the side not shown. An actuator 14 is rotatably and slidably mounted within housing 12 and includes an external knob 16 and a shaft 18 which extends into housing 12 through opening 20.

Figure 2:
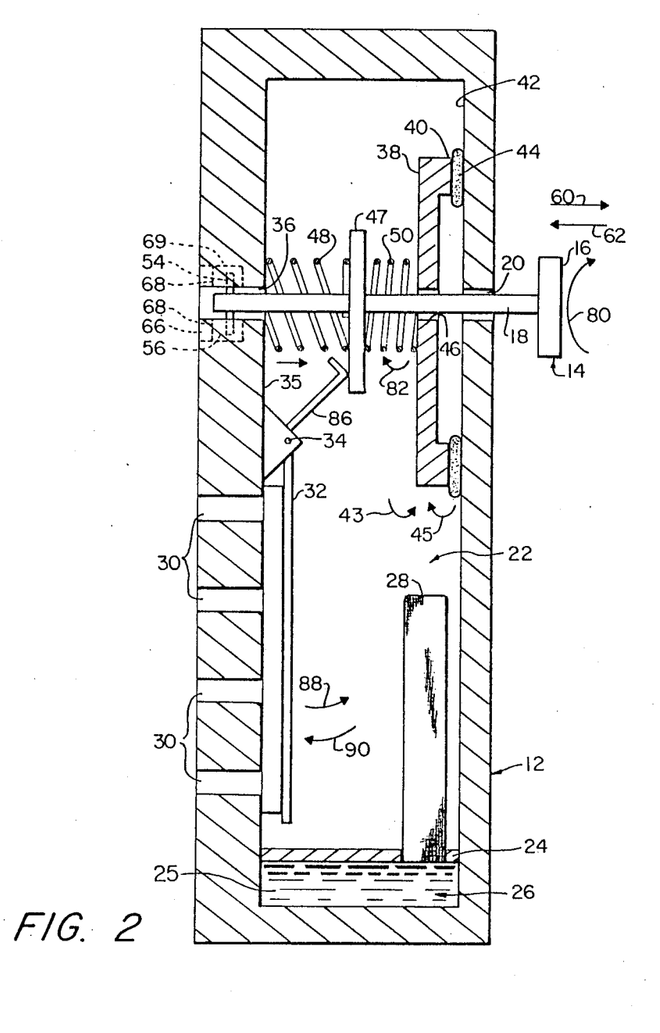
FIG. 2 is a cross-sectional view of the fluid dispenser taken along line 2—2 of FIG. 1 with the actuator in the first state.

The internal construction of mechanism 10 is shown in detail in FIG. 2. Housing 12 includes an inner chamber 22 within which is disposed a reservoir 26 containing a fragrance, insecticide or other volatile fluid 25. An absorbent wick 28 is mounted within chamber 22 with one end disposed through plate 24 into fluid 25. Wick 28 draws fluid from reservoir 26 and that fluid is subsequently emitted by the wick as a vapor. To provide adequate emission, wick 28 should have an exposed surface area of approximately several square inches. Fluid vapors are dispensed from dispenser 10 through ports 30 when the ports are opened to the outside air. Ports 30 are opened and closed by a closure 32 which is mounted by a pivot 34 to chamber wall 35 of housing 12 and is operated in a manner described more fully below.

Actuator shaft 18 extends through opening 20 and into opening 36 of housing 12. A circular rotor 38 includes a circumferential bearing surface 40 which is connected to chamber wall 42 by a visco-elastic adhesive 44. The adhesive permits rotor plate 38 to rotate relative to chamber wall 42 in the direction of arrows 43 and 45 while remaining attached to the chamber wall. Rotor 38 also includes a central hole 46 through which actuator shaft 18 extends.

A circular engagement plate 47 is attached to actuator shaft 18 approximately mid-way along the length of the shaft. Engagement plate 47 may be integral with shaft 18 or, alternatively, may be attached thereto by suitable adhesive, bolts or other attachment means. A helical compression spring 48 is wound about shaft 18 and is attached at one end to chamber wall 35 and at the other end to a first side of plate 47. A helical torsion spring 50 is likewise wound about shaft 18 and is attached at one end to a second side of plate 47 and at the other end to rotor 38.

Figure 3:
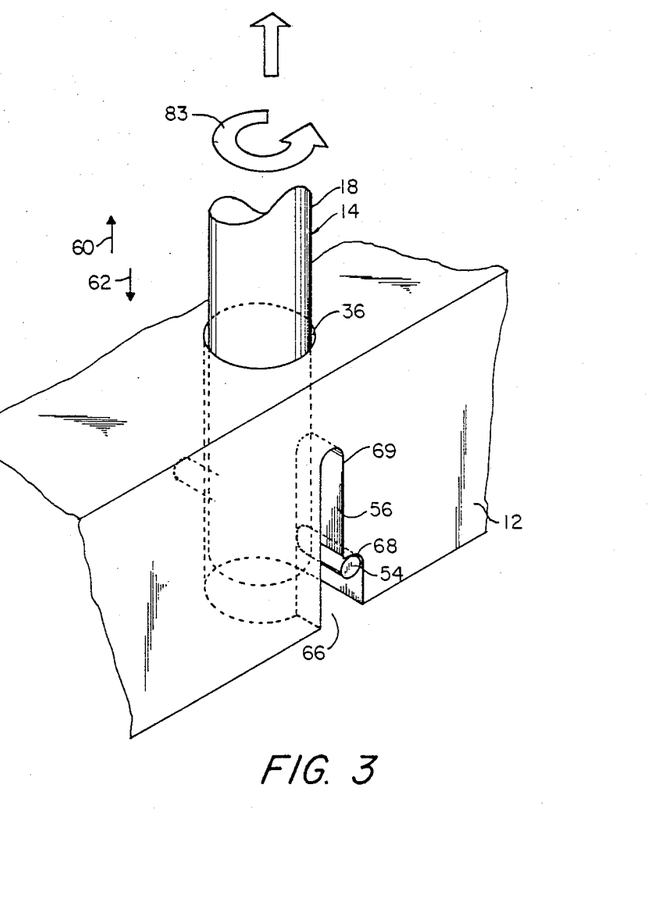
FIG. 3 is an enlarged axonometric view of the restraining means of FIG. 2.

As shown most clearly in FIG. 3, a retaining detent 54 is mounted through the lower end of shaft 18. Housing 12 includes a recess 56 which receives detent 54 and permits actuator 14 to slide back and forth within housing 12 in the direction of arrows 60 and 62, FIGS. 2 and 3. Recess 56, FIG. 3, includes an enlarged portion 66 proximate the outside of housing 12 which forms a shoulder 68 that engages and holds pin 54 when actuator 14 is retracted in the direction of arrow 62.

During periods when fluid dispensing is not required, the biasing force of compression spring 48, FIG. 2, urges plate 47 and actuator 14 in the direction of arrow 60 to remain in an extended condition. In this state detent 54 is received within narrow section 69 of slot 56 and does not engage shoulder 68. As a result, engagement plate 47 does not exert leverage on lever arm 86 and either gravity or a spring not shown biases closure 32 into a closed condition covering ports 30 and blocking emission of fluid 20.

Figure 4:
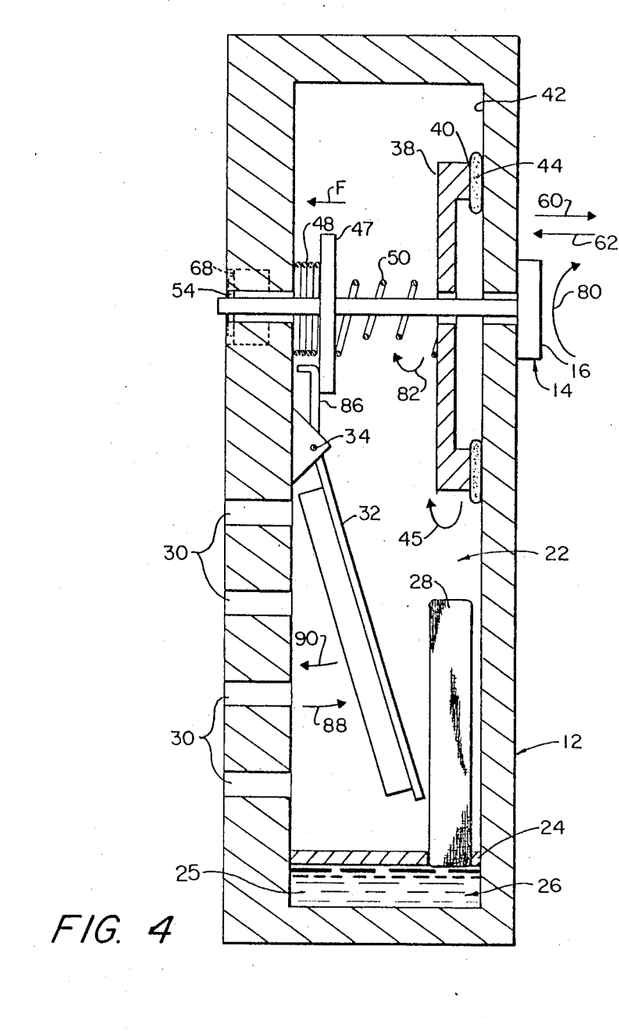
FIG. 4 is a view similar to that of FIG. 2 with the actuator in the second state.

In order to temporarily dispense fluid the operator grasps knob 16, rotates it clockwise in the direction of arrow 80 and depresses actuator 14 in the direction of arrow 62 into the position shown in FIG. 4. This operation winds spring 50 in the direction of arrow 82 and compresses spring 48. Wound spring 50 exerts a torque in the direction of arrow 82 which engages detent 54 with shoulder 68, as shown in FIGS. 3 and 4. As actuator 14 is retracted, plate 47 engages lever arm 86 of closure 32 and causes the closure to pivot open in the direction of arrow 88. Ports 30 are thereby uncovered and fluid from wick 28 is emitted through the ports. The ports remain open and emission continues for as long as detent 54 is restrained by shoulder 68 and actuator 14 remains in the retracted condition of FIG. 4.

Closure 32 covers the ports after a timed duration as follows. In the retracted condition of FIG. 4 torsion spring 50 is wound relatively tightly. As a result, the torque 83 it exerts on actuator shaft 18 keeps detent 54 engaged with shoulder 68. As long as sufficient torque is exerted spring 48 remains compressed and actuator 14 remains in the retracted condition. Wound torsion spring 50 also exerts a torque 82 on rotor 38 which causes the rotor to rotate relative to chamber wall 42 in the direction of arrow 45. This rotation is hindered and prolonged by visco-elastic adhesive 44 which joins rotor 38 and chamber wall 42. Eventually, after a time which is dependent upon the viscosity and stickiness of adhesive 44, rotor 38 rotates sufficiently in the direction of arrow 45 to unwind torsion spring 50. As a result, torque 83 is removed from actuator 14, detent 54 disengages shoulder 68 and the biasing force of spring 48 suddenly overcomes the restraining force and snaps actuator 14 in the direction of arrow 60 into the extended condition of FIG. 2. As a result, the leverage exerted by plate 47 on lever arm 86 is removed and closure 32 pivots downwardly in the direction of arrow 90 to reclose ports 30 and block fluid emission.

The time delay in the open state and hence the period of fluid emission may be increased by employing a stickier adhesive 44 which slows the movement of rotor 38 and unwinding of spring 50. Conversely, the time delay may be shortened by using a less viscous or sticky adhesive.

Figure 5:
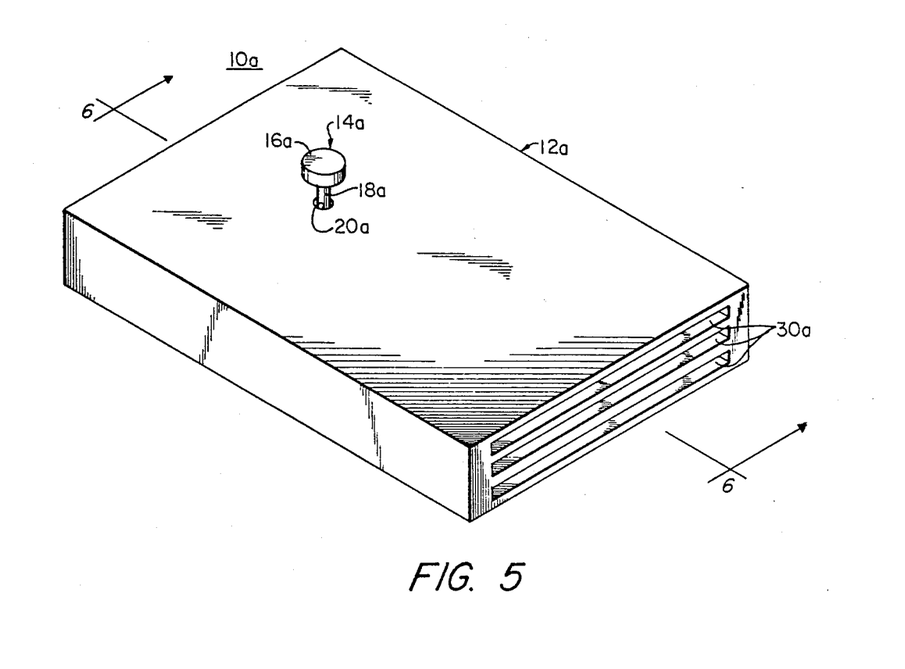
FIG. 5 is an axonometric view of an alternative fluid dispenser using the delayed actuator with visco-elastic timer of this invention.

An alternative dispenser 10a is shown in FIG. 5. Again, the dispenser includes a housing 12a and an actuator 14a which extends into the housing through an opening 20a. Actuator 14a includes an external knob and an elongate shaft 18a. A plurality of elongate ports 30a are disposed in one end of the housing.

Figure 6:
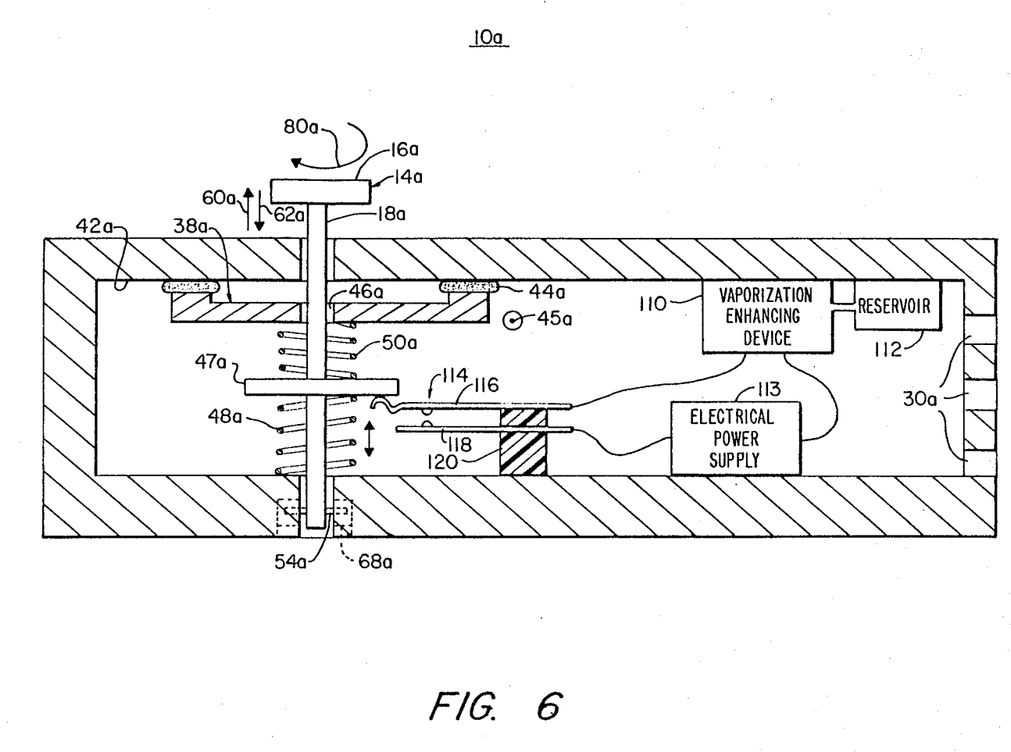
FIG. 6 is a cross-sectional view taken along line 6—6 of FIG. 5.

As shown in FIG. 6, dispenser 10a includes an actuator 14a, compression spring 48a, restaining detent 54a, shoulder 68a, torsion spring 50a, engagement plate 47a, rotor 38a, rotor central hole 46a and visco-elastic adhesive 44a which are constructed and operate identically to the components shown in the previous embodiment. Instead of a mechanical closure, however, dispenser 10a is provided with an electrically operated vaporization enhancing device 110 which when activated increases vaporization of fluid from reservoir 112. Device 110 may include, for example, a fan which utilizes motor-driven propellors or oscillating blades, an electrical resistance heater or an ultrasonic atomizer.

An AC or DC power source 113 is connected to device 110 through a switch 114. The switch includes a pair of normally open contacts 116 and 118 which are mounted on a support 120 within housing 12a.

With actuator 14a in the extended condition, compression spring 48a raises engagement plate 47a sufficiently so that contacts 116 and 118 remain open. As a result, vaporization enhancing device 110 remains shut off and no fluid is emitted through ports 30a.

To operate dispenser 10a for a timed duration knob 16a is grasped and rotated in the direction of arrow 80a and actuator 14a is depressed or retracted in the direction of arrow 62a so that detent 54a is engaged with shoulder 68a in the manner shown in FIG. 3. This winds torsion spring 50a to generate a torque on actuator 14a which engages detent 54a with shoulder 68a. As a result, actuator 14a and plate 47a are maintained in a retracted condition so that engagement plate 47a holds contacts 116 and 118 closed. This completes the electrical circuit and operates device 110 to enhance vaporization of fluid in reservoir 112. The vaporized fluid is then emitted through ports 30a.

The actuator switches back to the extended condition after the desired time delay in a manner similar to the prior embodiment. Torsion spring 50a urges rotor 38a to rotate relative to inner chamber wall 42a in the direction of arrow 45a. Due to visco-elastic adhesive 44a this rotation is very gradual. Eventually, spring 50a is unwound or relaxed by the rotation of rotor 38a and provides no torque to hold detent 54a in engagement with shoulder 68a. As a result, spring 48a suddenly snaps actuator 14a in the direction of arrow 60a back into the extended condition. Plate 47a is raised and contacts 116 and 118 again separate to open switch 114 and shut off vaporization enhancing device 110.

Figure 7:
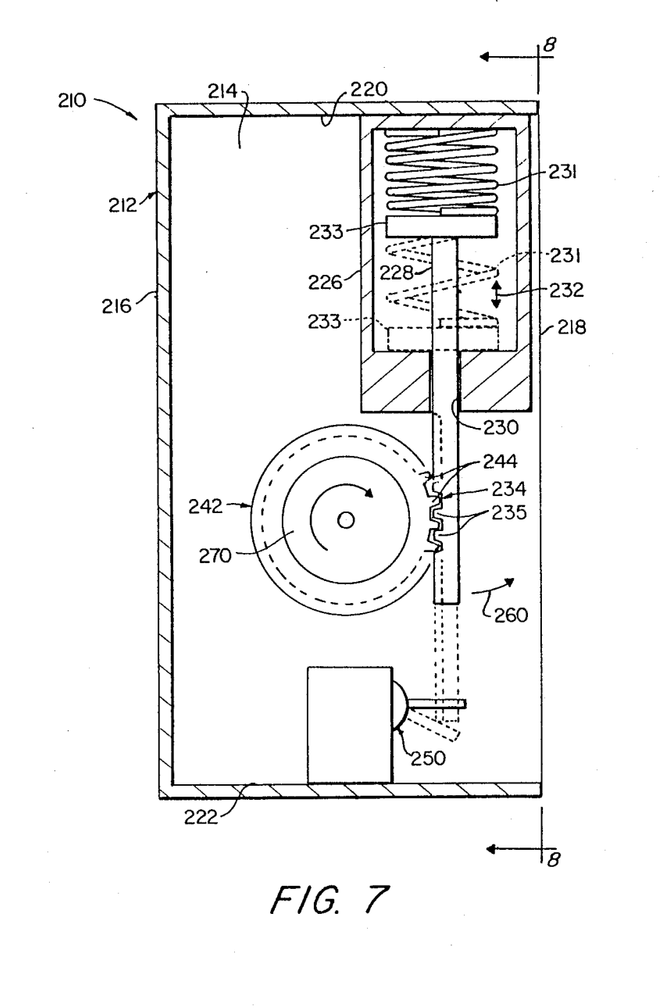
FIG. 7 is an elevational plan view of an alternative visco-elastic delayed timer according to this invention.
Figure 8:
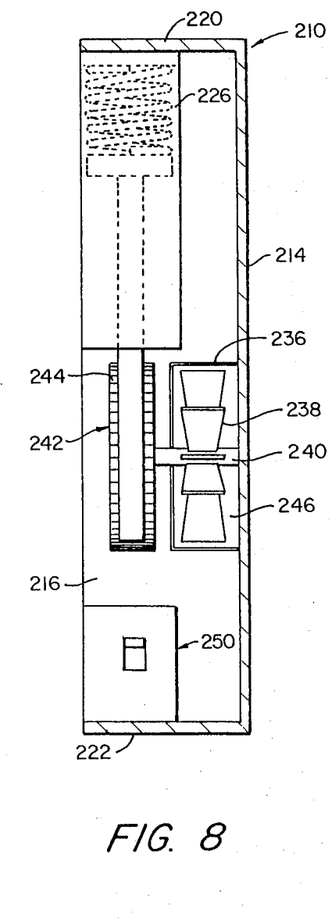
FIG. 8 is an elevational view taken along line 8—8 of FIG. 7.

An alternative timer 210 according to this invention is shown in FIGS. 7 and 8. The timer includes a support section 212 which is open in the front and includes a rear wall 214, side walls 216 and 218 and top and bottom walls 220, 222.

A guide 226 is attached to walls 218 and 220 such as by a suitable adhesive. An actuator 228 extends through a slot 230 in guide 226 and is slidable up and down in the directions of double-headed arrow 232. Actuator 228 carries a rack 234 below guide 226. A helical compression spring 231 is attached at one end to guide 226. The opposite end of spring 231 engages a knob 233 at the top of actuator 228. As shown in phantom, the compression spring urges actuator 228 into an extended condition so that knob 233 engages guide 226 adjacent to slot 230.

A compartment 236, FIG. 8, is attached by screws, bolts, adhesive or similar attachment means to wall 214 of support section 212. A paddle wheel device 238 is rotatably mounted by a shaft 240 to wall 214. Shaft 240 extends through compartment 236 and is attached axially to a pinion gear 242 having pinion teeth 244. A visco-elastic adhesive 246 fills compartment 236 and, interconnects the compartment with paddle wheel device 238.

A toggle switch 250 is mounted on bottom wall 222 of support section 212. Switch 250 includes resilient means, not shown, which urge the switch upwardly into an "on" condition. However, when the actuator is extended, as shown in phantom, switch 250 is depressed so that it switches into an alternative condition, e.g., an off state.

To operate timer 210, knob 233 is grasped and actuator 228 is retracted upwardly against spring 231. The actuator is composed of a flexible material so that it bends slightly in the direction of arrow 260. This enables rack teeth 235 to slide over pinion teeth 244. As a result, actuator 228 may be raised without having to rotate pinion gear 242 and paddle wheel device 238 against the resistance of viscous material 246 in compartment 236. In the retracted condition shown in FIG. 1, actuator 228 is spaced from toggle switch 250 and the switch maintains an on state. During the timed duration spring 231 urges actuator 228 downwardly so that rack teeth 235 engage and mesh with pinion teeth 244. This drives gear 242 in the direction of arrow 270 so that paddle wheel 238 turns within compartment 236. Visco-elastic adhesive 246 slows the rotation of paddle wheel 238 and pinion gear 242. Accordingly, the movement of rack 234 and actuator 228 in a downward direction is similarly delayed. The degree of this delay is determined by the viscosity of adhesive 246. A more viscous adhesive will cause slower movement of actuator 228 and, conversely, a less viscous adhesive will enable the actuator to extend more rapidly from guide 226.

Eventually, actuator 228 moves enough so that rack 234 extends beyond pinion gear 242; hence, rack teeth 235 disengage pinion teeth 244 and the rack and pinion no longer restrain or retard extension of actuator 228. The actuator abruptly switches to the fully extended position shown in phantom and as a result the bottom end of actuator 228 engages and depresses switch 250 and abruptly changes the switch to an "off" condition.

Although specific features of the invention are shown in some drawings and not others, this is for convenience only as each feature may be combined with any or all of the other features in accordance with the invention.

Other embodiments will occur to those skilled in the art and are within the following claims:

What is claimed is:

1. A delayed actuator mechanism with visco-elastic timer comprising:
   a support section;
   an actuator section mounted to said support section;
   biasing means for urging said actuator section into a first state and permitting said actuator section to be selectively switched to a second state;
   means for restraining said actuator section in said second state; and
   visco-elastic delay means for gradually releasing said means for restraining until said biasing means overcomes said means for restraining to abruptly switch said actuator section to said first state.

2. The mechanism of claim 1 in which said visco-elastic delay means includes a movable member and visco-elastic adhesive means interconnecting said movable member and said support section.

3. The mechanism of claim 2 in which said means for restraining includes means interconnecting said movable member and said actuator section, and responsive to said actuator section being switched into said second state for urging said movable member to move gradually relative to said support section until said biasing means suddenly overcomes said means for restraining to abruptly switch said actuator section to said first state.

4. The mechanism of claim 3 in which said means for restraining further includes a shoulder disposed in said support section and detent means carried by said actuator for engaging said shoulder and temporarily restraining said actuator section in said second state.

5. The mechanism of claim 4 in which said movable member includes a rotor and said means for urging includes torque biasing means responsive to said actuator being switched into said second state for applying torque to engage said detent with said shoulder and urging said rotor to rotate gradually relative to said support section to relax said torque biasing means until said biasing means suddenly overcomes said means for restraining to abruptly switch said actuator section to said first state.

6. The mechanism of claim 5 in which said torque biasing means includes a helical spring disposed about said actuator section.

7. The mechanism of claim 1 in which said actuator section is axially slidably mounted in said support section.

8. The mechanism of claim 6 in which said actuator section is axially rotatably mounted in said support section for rotating to wind said torque biasing helical spring in said second state.

9. The mechanism of claim 1 in which said biasing means includes a helical spring disposed about said actuator section and interconnecting said actuator section and said support section.

10. The mechanism of claim 1 in which said support section includes a housing.

11. The mechanism of claim 10 in which said housing includes a reservoir for containing a fluid and port means for dispensing said fluid.

12. The mechanism of claim 11, in which said port means has an area which is at least as large as the exposed area of said reservoir.

13. The mechanism of claim 11 further including means responsive to said actuator section in one of said first and second states, for accelerating vaporization of said fluid in said reservoir.

14. The mechanism of claim 13 in which said means for accelerating includes a set of electrical contacts which are closed in response to said actuator section being in one of said first and second states to drive said means for accelerating and opened in response to said actuator section being in the other said state to stop said means for accelerating.

15. The mechanism of claim 11 further including closure means for covering said port means in response to said actuator means being in one of said first and second states and uncovering said port means in response to said actuator means being in the other said state.

16. The mechanism of claim 15 in which said closure means is pivotably mounted to said housing.

17. The mechanism of claim 1 in which said means for restraining includes first gear means operably connected to said visco-elastic delay means and complementary second gear means connected to said actuator section and responsive to said biasing means for driving said first gear means until said second gear means disengages said first gear means and said actuator section is abruptly switched to said first state.

18. The mechanism of claim 17 in which said first gear means includes a rotatable pinion gear.

19. The mechanism of claim 17 in which said second gear means includes rack means arranged longitudinally on said actuator section.

20. The mechanism of claim 2 in which said support section includes compartment means and said movable member is movably mounted in said compartment means and said visco-elastic adhesive means is disposed in said compartment means about said movable member for delaying movement of said movable member.

21. The mechanism of claim 1 in which said biasing means includes helical spring means disposed between said support section and said actuator section.

22. The mechanism of claim 20 in which said movable member is rotatably mounted in said compartment means.

23. The mechanism of claim 20 in which said means for restraining includes pinion gear means axially connected with said rotatably movable member for rotating therewith and complementary rack means connected to said actuator section and responsive to said biasing means for driving said pinion gear means until said rack means disengages said pinion gear means and said actuator section is abruptly switched to said first state.

24. The mechanism of claim 22 in which said movable member includes a paddle wheel device.

25. The mechanism of claim 23 in which said actuator section is flexible for permitting said rack means to slide over said pinion means as said actuator section is switched from said first state to said second state.

26. A delayed fluid dispenser with visco-elastic timer comprising:
a support section having a reservoir for containing a fluid and port means for dispensing said fluid;
an actuator section mounted to said support section;
biasing means for urging said actuator section into a first state and permitting said actuator section to be selectively switched to a second state;
means for temporarily restraining said actuator section in said second state;
visco-elastic delay means for gradually releasing said means for restraining until said biasing means overcomes said means for restraining to abruptly switch said actuator section to said first state; and
means responsive to said actuator section in one of said first and second states for accelerating vaporization of said fluid in said reservoir and dispensing of said fluid through said port means.

27. The dispenser of claim 26 in which said means for accelerating vaporization includes fan means for increasing air flow across said reservoir.

28. The dispenser of claim 26 in which said means for accelerating vaporization includes a heating element for increasing the temperature of the fluid in said reservoir.

29. The dispenser of claim 26 in which said means for accelerating vaporization includes means for atomizing the fluid.

30. A delayed fluid dispenser with visco-elastic timer comprising:
a support section having a reservoir for containing a fluid and port means for dispensing said fluid;
an actuator section mounted to said support section;
biasing means for urging said actuator section into a first state and permitting said actuator section to be selectively switched to a second state;
means for restraining said actuator section in said second state;
visco-elastic delay means for gradually releasing said means for restraining until said biasing means overcomes said means for restraining to abruptly switch said actuator section to said first state; and closure means for closing to cover said port means in response to said actuator means being in one of said first and second states and opening to uncover said port means in response to said actuator means being in the other said state.

31. A delayed actuator mechanism with visco-elastic timer comprising:

a support section;

an actuator section mounted to said support section;

biasing means for urging said actuator section into a first state and permitting said actuator section to be selectively switched to a second state;

means for restraining said actuator section in said second state; and visco-elastic delay means for gradually releasing said means for restraining until said biasing means overcomes said means for restraining to abruptly switch said actuator section to said first state; and said means for restraining including first gear means operably connected to said visco-elastic delay means and complementary second gear means connected to said actuating section and responsive to said biasing means for driving said first gear means until said second gear means disengages said first gear means and said actuator section is abruptly switched to said first state.

* * * * *